(12) United States Patent
Harris

(10) Patent No.: US 9,113,625 B2
(45) Date of Patent: Aug. 25, 2015

(54) ADJUVANT FOR AGRICULTURAL CHEMICALS

(75) Inventor: Michael Claude Harris, Hahira, GA (US)

(73) Assignee: CJB Industries, Inc., Valdosta, GA (US)

( * ) Notice: Subject to any disclaimer, the term of this patent is extended or adjusted under 35 U.S.C. 154(b) by 799 days.

(21) Appl. No.: 13/498,341

(22) PCT Filed: Sep. 9, 2010

(86) PCT No.: PCT/US2010/048218
§ 371 (c)(1),
(2), (4) Date: May 15, 2012

(87) PCT Pub. No.: WO2011/041079
PCT Pub. Date: Apr. 7, 2011

(65) Prior Publication Data
US 2012/0225783 A1    Sep. 6, 2012

Related U.S. Application Data

(60) Provisional application No. 61/247,089, filed on Sep. 30, 2009, provisional application No. 61/287,313, filed on Dec. 17, 2009.

(51) Int. Cl.
*A01N 25/00*    (2006.01)
*A01N 25/02*    (2006.01)
*A01N 47/24*    (2006.01)

(52) U.S. Cl.
CPC ............... *A01N 25/02* (2013.01); *A01N 47/24* (2013.01)

(58) Field of Classification Search
None
See application file for complete search history.

(56) References Cited

U.S. PATENT DOCUMENTS

| 2002/0123430 A1 | 9/2002 | Xu et al. |
| 2004/0097372 A1 | 5/2004 | Abraham et al. |
| 2004/0138176 A1 | 7/2004 | Miles |

FOREIGN PATENT DOCUMENTS

| JP | 2007-262051 | 10/2007 |
| WO | WO-99/29171 | 6/1999 |

OTHER PUBLICATIONS

International Search Report and Written Opinion for PCT App. No. PCT/US2010/048218 mailed May 24, 2011.

*Primary Examiner* — Alton Pryor
(74) *Attorney, Agent, or Firm* — Womble Carlyle Sandridge & Rice, LLP; Mark D. Jenkins

(57) ABSTRACT

The present invention provides adjuvant chemical compositions that increase the effectiveness of a wide array of agricultural chemicals. Specifically, the present adjuvant compositions may increase the effectiveness of the normal, accepted amounts of an agricultural chemical per acre. Alternatively, the present adjuvant compositions may obtain similar results upon application of a decreased amount an agricultural chemical per acre. Compositions are also provided that comprise, in addition to the adjuvant compositions, at least one agricultural chemical. The present invention further provides methods of preparation and use thereof.

45 Claims, No Drawings

ADJUVANT FOR AGRICULTURAL CHEMICALS

BACKGROUND OF THE INVENTION

The present invention relates generally to agricultural chemical compositions. More specifically, the present invention relates to agricultural adjuvant chemical compositions for enhancing the effectiveness of agricultural chemicals.

Research efforts continue to focus on achieving the maximum effectiveness of various agricultural chemicals. The effectiveness of agricultural chemicals is difficult to attain particularly when the approach results in lower concentrations or rates of application. Further, environmental regulations limit the amount of certain agricultural chemicals, such as pesticides, that can be applied to plants. Thus, achieving enhancement of existing agricultural chemicals at safe levels is extremely beneficial to the agricultural industry.

SUMMARY OF THE INVENTION

The present invention provides adjuvant chemical compositions that increase the effectiveness of a wide array of agricultural chemicals. Specifically, the present adjuvant compositions may increase the effectiveness of the normal, accepted amounts of an agricultural chemical per acre. Alternatively, the present adjuvant compositions may obtain similar results upon application of a decreased amount an agricultural chemical per acre.

The adjuvant compositions may comprise at least one permeabilizing agent, flow agent, acid, surfactant, biocide, antifoaming agent, surface active compound such as a block polymer, emulsification agent, base, stabilizer, thickener, water, or preservative. The adjuvant compositions further comprise at least one alkylamine. Compositions are also provided that comprise, in addition to the adjuvant composition, at least one agricultural chemical including, but not limited to chemicals for pest control, herbicidal control, fungicidal control or plant growth regulation. The remainder of both compositions comprises water. The present compositions may be in solid or liquid form. The present invention further provides methods of preparation and uses thereof.

Additional advantages of the invention will be set forth in part in the detailed description, which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory of preferred embodiments of the invention, and are not restrictive of the invention, as claimed.

DETAILED DESCRIPTION OF THE INVENTION

The present invention provides agricultural adjuvant chemical compositions that may increase the effectiveness of a wide array of agricultural chemicals. An adjuvant is a chemical or combination of chemicals which increases the effectiveness of at least one primary active ingredient or chemical. In one embodiment, the adjuvant compositions result in quicker, more efficient action on behalf of the chosen agricultural chemical (i.e., active component). In one embodiment, the adjuvant compositions may be combined with an active agricultural chemical at the time of application (e.g., tank mix) that results in the use of lower amounts of active agricultural chemical. In one embodiment, the adjuvant compositions result in improved results at the same level of active agricultural chemical. In one embodiment, compositions are provided that comprise, in addition to at least one adjuvant composition, at least one agricultural chemical including, but not limited to chemicals for pest control, herbicidal control, fungicidal control or plant growth regulation.

Without being bound by any particular theory, the applicant believes that the addition of permeabilizing agents to the at least one agricultural chemical results in improved permeability through the plant cell wall, which, in turn, results in improved efficacy of a large variety of active components such as, for example, agricultural chemicals. The permeabilizing agents interact at sites on the outer membrane surface, at which divalent cations crossbridge adjacent lipopolysaccharide molecules and is believed to cause a destabilization of the outer membrane that permits uptake of the agricultural chemical or other molecules in the cell environment or both active and other molecules. The permeabilizing agent promotes uptake by affecting the lipopolysaccharide or divalent cationic crossbridge and further assists with the molecular transport of the active component across membranes within the cell and from cell to cell.

In one embodiment, the adjuvant compositions include at least one permeabilizing agent alone or in combination with other permeabilizing agents. In one embodiment, the adjuvant compositions can be supplied as a solid or a liquid, including thixotropic droplets. In one embodiment, the solid can be a granule or a powder. In one embodiment, the liquid can be a solution, dispersion or suspension in water or other carrier. In one embodiment, these products are generally diluted into water before being sprayed onto the field from either an airplane or ground application equipment. In one embodiment, solid formulations can be combined with wetting agents or surfactants for better deposition or application on the plants surface or substitute and better uptake by the plant. In a preferred embodiment, solid formulations are utilized due to higher loading levels.

In one embodiment, the at least one permeabilizing agent functions by improving the permeability of the cell walls of the plant or plants to which it is applied. By improving the permeability of the cell walls, the active components have better penetration into the plant. Also, in the case of insects, bacteria, fungi, viruses and acaricides, the at least one permeabilizing agent can improve the permeability of the cell walls of these agents and improve the passage of the active components into these biological entities, thus improving the efficacy of these compounds. Increased efficacy can translate into lower effective dosages, which is a tremendous benefit, particularly with governmental regulations constantly lowering the permitted dosages of these compounds. Further, as the chosen active agricultural chemical penetrates the plant cell wall, the resulting adjuvant compositions are more persistent than active components applied topically to plants that do not effectively penetrate the plant cell wall. Accordingly, an insect that attempts to ingest a plant, where the plant has an effective amount of an insecticide present inside the cell wall, may die long after conventional topically applied insecticides would be washed away.

In one embodiment, the at least one permeabilizing agent is at least one chelating agent. A chelate, sometimes referred to as a sequestrant, a complex ion, or a coordination compound, can be an organic compound that combines with a metal ion to form a complex in which the donor atoms are connected to each other as well as to the metal in one embodiment. Thus, in one embodiment, the metal becomes part of a heterocyclic ring. In one embodiment, donor atoms in the chelate complex may be tied together with additional chelate rings so that each chelating agent may contain two, three, four, five, six or even more donor groups. In a preferred embodiment, the chelating agent is ethylenediaminetetraacetic acid (EDTA), diethylenetriaminepentaacetic acid (DTPA), (hydroxyethyl)ethylenediaminetriacetic acid (HEDTA), nitrilotriacetic acid (NTA), oxalic acid, citric acid, or a combination thereof. A particularly preferred chelate is EDTA, which has two amine donor groups and four carboxyl donor groups. In one embodiment, EDTA supplies the complete requirements for the coordination sphere of many metals with a single molecule where it might take three molecules of ethylenediamine to meet the same-requirements. A chelating agent that supplies two donor electrons to the metal is said to be bidentate. Similarly ter-, quadri, quinqui-, and sexadentate donors, bind the metal in 3, 4, 5, and 6 positions, respectively. Hence, EDTA is sexadentate and ethylenediamine is bidentate, for example.

In one embodiment, the adjuvant composition comprises EDTA tetrasodium in an amount of between 0.1% and 40% by weight. In a particularly preferred embodiment, the adjuvant composition comprises EDTA tetrasodium in an amount of about 20%.

In one embodiment, the at least one chelating agent can combine with a metal ion to form soluble complexes that aid the ions in movement across barriers. Suitable non-limiting examples include the use of humic acids by plants to dissolve trace elements and make them accessible. In an alternative embodiment, the at least one chelating agent acts to remove ions from solution or make transport more difficult.

In one embodiment, chelating agents or mixtures of thereof include, but are not limited to sugars, amino acids, organic diacids, diamines, alpha ketoacids, alphahydroxyacids, aminodiacids, amino triacids, amino tetraacids, tdol amines, and organic polyacids and their sodium, potassium, and ammonium salts. Specific non-limiting examples of these chelating compounds include, but are not limited to the sugars, acids and salts of maleic acid, malonic acid, tartaric acid, citric acid, glycine, lactic acid, malic acid, succinic acid, oxalic acid, dextrose, ethylenediaminetetraacetic acid (EDTA), tris(hydroxymethyl)aminomethane, lactose, mannitol, glutaric acid, malic acid, succinic acid, glycerol, humic acid, fulvic acid, sorbic acid, sorbose, ethylene diamine, 1,2 diaminocyclohexane, trimethylenediamine, tetramethylenediamine, 1,2 diaminopropane, diethylenetriamine, triethylenetetramine, triaminodiethylamine, N-hydroxyethylethylenediamine, sodium polyphosphate, potassium polyphosphate, ammonium polyphosphate, sodium hexametaphosphate and mixtures thereof. In one embodiment, the at least one chelating agent used in the present compositions can be 100% of any particular chelator, or a combination of chelator in any ratio. In one embodiment, a combination or mixture of chelating compounds may dissolve faster than a single compound. In a preferred embodiment, 100% oxalic acid, 100% citric acid, 100% EDTA, and combinations of these are utilized. In a particularly preferred embodiment, the adjuvant composition comprises between 0.1% and 20% of citric acid based on total formulation weight. Preferably, the adjuvant composition comprises about 8.0% of citric acid.

In one embodiment, the at least one chelating agent is believed to function by sequestering divalent metal ions and keeping them from ordering the lipopolysaccharide layer in the plant cell walls. The voids may then be filled with phospholipids which are much more permeable. In one embodiment, the activity of some chelating agents is enhanced by amines and other cationic substances, such as tris, ethylamine, propylamine, diethanolamine, and 3-aminopropanol.

In one embodiment, the at least one permeabilizing agent can be any cationic compound capable of permeabilizing the plant cell wall. In one embodiment, cationic compounds, for example, polycationic compounds and cationic surfactants alter the ordering of the lipopolysaccharide layer in plant cell walls by replacing the divalent cationic bridging metal ions. In one embodiment, the negatively charged lipopolysaccharide layer which normally binds to the positively charged metals binds to the much bulkier cationic amines creating gaps in the lipopolysaccharide layer. In one embodiment, the cationic compound is a polycationic compound, for example, a polyamine such as (diethylenetriamine, triethylenetetramine, tetraethylenepentamine, and polyethylene polyamine N-oleylamine polyhexamethamine polyamine).

In one embodiment, quaternary ammonium salts are utilized in the adjuvant compositions. Suitable non-limiting examples include cocodimethyl and dicocodimethylammonium chloride, as are other coco-substituted quaternary ammonium salts. Suitable non-limiting examples of tertiary amines that can be used include tertiary amines including linear alkyl groups or a linear alkenyl groups with a carbon number of 8 to 20, and can be derived from natural oil or fat, and can also include one or more an oxyalkylene groups. Preferred tertiary amines include mono-long-chain alkylamine, for example, bis(2-hydroxyethyl)cocoamine, bis(2-hydroxyethyl)-tallowamine, bis(2-hydroxyethyl)oleylamine, and bis(2-hydroxyethyl)laurylamine. In another embodiment, suitable non-limiting examples include polyoxyalkylenated long-chain alkylamine, for example, bis(polyoxyethylene(EOp=3 to 30))cocoamine, bis(polyoxyethylene (EOp=3 to 30))tallowamine, bis(polyoxyethylene(EOp 3 to 30))oleylamine, bis(polyoxyethylene(EOp=3 to 30))laurylamine, bis(polyoxyethylene(EOp=3 to 30))palmstearylamine, bis(polyoxyethylene(EOp=3 to 10)polyoxypropylene-(POp=3 to 10)cocoamine, and bis(polyoxyethylene (EOp=3 to 10)polyoxypropylene (POp=3 to 10)tallowamine. In the compounds described above, EOp represents an average addition mole number of ethylene oxide, and POp represents an average addition mole number of propylene oxide.

In one embodiment, the adjuvant composition comprises at least one alkylamine. In one embodiment, the adjuvant composition comprises at least one fatty acid amine. In a preferred embodiment, the adjuvant composition comprises a combination of cocoalkylamines in an amount of between 0.1% and 10% by weight. In a particularly preferred embodiment, the adjuvant composition comprises about 2% by weight of a combination of cocoalkylamines such as that marketed as ARMEEN DMCD and manufactured by Akzo Nobel of Chicago, Ill.

In a preferred embodiment, the adjuvant compositions comprise at least one quaternary ammonium surfactant. In one embodiment, the adjuvant compositions comprise at least one quaternary ammonium surfactant such as that marketed as ARQUAD 2C-75 and manufactured by Akzo Nobel of Chicago, Ill. Preferably, the at least one quaternary ammonium surfactant is present in an amount of between 0.1% and 40% based on total weight of the formulation.

In one embodiment, derivatives of tertiary amines can be utilized alone or in combination with at least one other permeabilizng agent. Suitable non-limiting examples of these derivatives include amine salts, quaternized products, betaines, and amine oxides. In one embodiment, the tertiary amine salts include salts of inorganic acids such as hydrochloric acid and sulfuric acid, and salts of organic acids such as acetic acid. In particular, hydrochlorides and acetates are preferred. In one embodiment, the quaternized products of the tertiary amines described above can be obtained by using known quaternizing agents. The quaternizing agents include dialkylsulfuric acids (an alkyl group having a carbon number of 1 to 3) and halogenated alkyl (an alkyl group having a carbon number of 1 to 3, a benzyl group).

In one embodiment, the quaternary salts are advantageously methyl chloride-quaternized products, benzyl chloride-quaternized products, dimethylsulfuric acid-quaternized products and diethylsulfuric acid quaternized products of the tertiary amines described above. In a particularly preferred embodiment, the quaternary ammonium salts include quaternized long-chain amines, tri-lower alkyl long-chain alkylammonium chloride, trimethylcocoammonium (coco=$C_{12}$ to $C_{15}$ alkyl) chloride, trimethyloctadecylammonium chloride, dialkyldi-lower alkylammonium chloride, dimethyldioctadecylammonium chloride, dimethyldicocoalkylammonium chloride, quaternized polyoxyalkylenated long-chain amines, alkyldi(polyoxyethylene)lower alkylammonium chloride, methylbis(omegahydroxypoly(oxyethylene)-oleo) ammonium chloride in which polyoxyethylene is derived from 2 to 30 moles of ethylene oxides.

In one embodiment, the adjuvant composition comprises at lease one amine oxide derived from the tertiary amines. Suitable non-limiting examples include trialkylamine oxide, lauryldimethylamine oxide, stearyldimethylamine oxide, dihydroxyethylalkylamine oxide, dihydroxyethyloctylamine oxide, dihydroxyethyldodecylamine oxide, dihydroxyethyltallowlamine oxide, di(polyoxyethylene)alkylamine oxide, bis(polyoxyethylene)tallowamine oxide, bis(polyoxyethylene) cocoamine oxide, bis(polyoxyethylene)dodecylamine oxide, lower alkylpolyoxyethylenealkylamine oxide, methylpolyoxyethylenecocoamine oxide. In one embodiment, the amines or derivatives thereof are blended into the composition in a proportion of 10% to 30%. In a preferred embodiment, the amines or derivatives thereof are blended into the composition in an amount of about 15% to 25 weight % based on total weight of the formulation.

In one embodiment, the at least one permeabilizing agent can further comprise any anionic compound capable of permeabilizing the plant cell wall. In one embodiment, the anionic compound is an anionic surfactant or a polyanionic compound, for example, a polymer such as a polyacid such as polylactic acid, polyphosphates and polyacrylates, or monomers such as citric acid EDTA and others listed above. In another embodiment, anionics which remove calcium (e.g., sulfate ion) and form insoluble calcium sulfate can be utilized. Usable forms of sulfate ion include, but are not limited to, ammonium sulfate, sodium sulfate, potassium sulfate, hydrogen sulfate or any mixture thereof.

In one embodiment, at least one zwitterionic compound is utilized as a chelating agent. In one embodiment, the at least one zwitterionic compound includes both a positive and a negative charge on the same molecule. Suitable non-limiting examples include amino acids and polyamine polycarboxylic acids, betaines derived from the tertiary amines which include trialkylbetaines, long-chain alkyldi-lower alkylbetaines such as lauryldimethylbetaine, stearyldimethylbetaine, cocodimethylbetaine, and decyldimethylbetaine.

In one embodiment, calcium and magnesium salts can also serve as a permeabilizing agent. In one embodiment, calcium and magnesium salts function in the opposite way from chelators or amines in that they provide too much rigidity to a cell wall and it becomes brittle and hence more permeable. In one embodiment, soluble salts such as calcium and magnesium chlorides, nitrates, sulfites, thiosulfates, nitrite, bisulfites, or salts of organic compounds such as calcium or magnesium lactate, or citrate, may be utilized.

In one embodiment, combinations of chelating agents and cationic compounds can be utilized. Combinations of oxalic acid and citric acid are particularly preferred due to its action as an effective permeabilizer without exhibiting toxicity on exposure. In one embodiment, citric acid lowers oxalic acid toxicity and also functions as a permeabilizer. Combinations of chelators and quaternary ammonium salts are also particularly preferred.

In one embodiment, the at least one permeabilizing agent and, optionally, agricultural chemical, are provided in an aqueous solution. In one embodiment, other water-miscible solvents can also be used, typically in concentrations of less than 25% by volume. These solvents include, but are not limited to, $C_{1-5}$ alcohols such as ethanol, propanol and isopropyl alcohol, polyhydric alcohols such as glycerol, pentaerythritol, and the like, dimethyl sulfoxide, dimethyl formamide, glymes, acetone and the like. Crop oils can also be used.

In one emobdiment, the agricultural adjuvant chemical compositions may be added to or mixed with at least one agricultural chemical at the time of application. In one embodiment, compositions are provided that may comprise the adjuvant chemical composition in combination with at least one or a combination of agricultural chemicals which results in a desired effect on a plant. In a preferred embodiment, a composition comprises at least one acidic compound, at least one basic compound, at least one permeabilizing agent, at least one alkylamine and at least one agricultural chemical. In a preferred embodiment, the remainder of the adjuvant chemical composition comprises water. In one embodiment, the agricultural chemical is at least one pesticide. In one embodiment, the at least one agricultural chemical is at least one fungicide, herbicide or pesticide that includes any substance that will prevent, destroy, repel, or mitigate any pest, or that functions as a plant regulator, desiccant or defoliant.

In one embodiment, the agricultural chemical is at least one insecticide that is effective against a particular insect to be eliminated from a particular crop or site can be used. Suitable non-limiting examples of pyrethroid type insecticides include Fenvalerate (alpha-cyano-3-phenoxybe-nzyl-2-(4-chlorophenyl)-3-methylbutanoate) and Baythroid (cyano-4-fluoro-3-phenoxybenzyl-3-(2,2-dichlorovinyl)-2,2-dimethylcyclopr-opanecarboxylate). Suitable non-limiting examples of organic phosphorus type insecticides include DDVP (2,2-dichlorovinyldimethyl phosphate), Sumithion (MEP) (dimethyl 4-nitro-m-tolyl phosphorothioate), Malathion (S-1,2-bis(ethoxycarbonyl)et-hyldimethyl phosphorodethioate), Dimethoate (dimethyl S-(N-methylcarbamoylmethyl) phosphorodithioate), Elsan (S-[alpha-(ethoxycarbonyl)benzyl]dimethyl phosphorodithioate), and Baycid (dimethyl 4-methylthio-m-tolyl phosphorothioate). Carbamate type insecticides include Bassa (O-sec-butylphenyl methylcarbamate), MTMC (m-tolylmethylcarbamate), Meopal (3,4-dimethylphenyl-N-methylcarbamate), and NAC (1-naphthyl methylcarbamate), and Methomyl (S-methyl-N-(methylcarbamoyloxy)thioacetimidate), and Cartap (SS'-2-dimethylamino trimethylene bis-(thiocarbamate)), for example. Suitable natural insecticides include pyrethrin preparations and piperonyl butoxide preparations which originate from *Chrysanthemum cinerariaefolium,* rotenone preparations (originate from Derris which is a shrub of the pulse family), and nicotine preparations originating in derris shrubs of Family Legumoinosae (3-(1-methyl-2-pyrrolidinyl)pyridine sulfate).

In one embodiment, the agricultural chemical may comprise at least one herbicide alone or in combination with other herbicides. In one embodiment, the at least one herbicide causes the desired result. In one embodiment, the agricultural chemical may comprise at least one post-emergent herbicide.

In one embodiment, suitable non-limiting examples include bipyridyliums, diphenyl ethers (nitrophenyl ethers), triazines, uracils, phenylureas, or nitriles. Other suitable non-limiting examples include acid amide-based herbicides such as Stam (3',4'-dichloropropionanilide, DCPA) and Alachlor (2-chloro-2',6'-diethyl-N-(methoxymethyl)-acetanilide).

Suitable non-limiting examples of urea-based herbicides include DCMU (3-(3,4-dichlorophenyl)-1,1-dimethylurea) and Rinuron (3-(3,4-dichlorophenyl)-1-methoxy-1-methylurea). Suitable non-limiting examples of sulfonyl urea-based herbicides include thifensulfuromnethyl(methyl-3-(4-methoxy-6-methyl-1,3,5-triazin-2-ylcarbamoylsulfamoyl)-2-tanoate) and Flazesulfuron (1-(4,6-dimethoxy pyrimidin-2-yl)-3-(3-trifluoromethyl-2-pyridylsulfonyl-)urea). Suitable non-limiting examples of dipyridyl-based herbicides include Paraquat dichloride (1,1'-dimethyl-4,4'-bipyridinium dichloride) and Diquat dibromide (6,7-dihydrodipyride[1,2-a:2',1'c]-pyrazinediium dibromide). Suitable non-limiting examples of diazine-based herbicides include Bromacil (5-bromo-3-sec-butyl-6-methyluracil). Suitable non-limiting examples of S-triazine-based herbicides include Gesatop (2-chloro-4,6-bis(ethylamino)-1,3,5-triazine) and Simetryn (2,4-bis(ethylamino)-6-methylthio-1,3,5-triazine). An example of a nitrile-based herbicide includes DBN (2,6-dichlorobenzonitrile-). Suitable non-limiting examples of dinitroaniline-based herbicides include Trifluralin (alpha,alpha, alpha-trifluoro-2,6-dinitro-N,N-dipropyl-p-toluidine). Suitable non-limiting examples of carbamate-based herbicides include Thiobencarb (Saturn) (S-p-chlorobenzyl diethylthiocarbamate) and MCC (methyl-3,4-dichlorocarbe-nylate. NIP (2,4-dichlorophenyl-p-nitro-phenyl ether) is an example of a diphenyl ether-based herbicide. PCP (sodium pentachlorophenoxide) is an example of a phenol-based herbicide. MDBA (3,6-dichloro-2-methoxybenzoic acid dimethylamine salt) is an example of a benzoic acid-based herbicide. Suitable non-limiting examples of phenoxy-based herbicides include 2,4-D sodium salt (sodium 2,4-dichlorophenoxyacetate), 2,4 D Esters, and Mapica ([4-chloro-o-toluyl)oxy]aceto-o-chloroanilide. Suitable non-limiting examples of organic phosphorus-based herbicides include Glyphosate (N-(phosphonomethyl)glycinate, Bialaphos (sodium salt of L-2-amino-4-[(hydroxy(methyl)phosphi-noyl]-butylyl-alanyl-N-alanine), and Glufosinate (ammonium DL-homoalanin-4-yl(methyl)phosphinate). TCA sodium salt (sodium trichloronate) is an example of an aliphatic group-based herbicide. In one embodiment, hydrogen peroxide is a suitable herbicide.

In one embodiment, the dipyridyl-based herbicides and the organic phosphorus-based herbicides are preferred. In another embodiment, the organic phosphorus-based herbicides are more preferred, and Bialaphos (sodium salt of L-2-amino-4-[hydroxy)(methyl)phosphinoyl]butyl-L-alanyl-N-alanine), Glufosinate (ammonium DL-homoalanin-4-yl (methyl)phosphinate), or Glyphosate (N-(phosphonomethyl) glycinate) are particularly preferred.

In one embodiment, one or more auxin growth regulators may be used alone or in combination as the at least one agricultural chemical. Suitable non-limiting examples of auxin growth regulators include phenoxy, benzoic acid derivatives, or picolinic acid derivatives. In one embodiment, one or more amino acid inhibitors may be used alone or in combination within the adjuvant composition. Suitable non-limiting examples include, glyphosate, sulfosate, sulfonyl ureas, imidazolinones, or sulfonanalides.

In one embodiment, the agricultural chemical comprises at least one plant growth regulator. In one embodiment, the at least one plant growth regulator may be any compound that regulates plant growth can be included in the compositions of the invention. Non-limiting examples of the plant-growth regulator include, but are not limited to, defoliators and desiccants. Specific non-limiting examples include MH (maleic hydrazide), ethephon (2-chloroethylphosphonic acid), Folex (S,S,S, tributyl phosphorothioate, Dropp (thidiazuron), Pix (mepiquat chloride). In one embodiment, any defoliating compound that is effective at defoliating a desired plant can be used. Suitable non-limiting examples of suitable defoliating agents include paraquat, diquat, endothall, chlorates, ethephon, tributylyphosphorthoate, cacodylic acid and its sodium salt, MSMA, diuron, dimethipin, monocarbamide, carfentrazone, cyclanalide and thidiazuron.

In one embodiment, the agricultural chemical is at least one insect growth regulator. Suitable non-limiting examples include Diflubenzuron (1-(4-chlorophenyl)-3-(2,6-difluorobenzoyl)urea), Teflubenzuron (1-[3,5-dichloro-2,4-difluorophenyl)-3-(2,6-difluo-robenzoyl)urea), Chlorfluazuron (1-[3,5-dichloro-4-(3-chloro-5-trifluorom-ethyl-2-pyridiloxyphenyl]-3(2,6-difluorobenzoyl)urea, Buprofezin (2-tert butylimino-3-isopropyl-S-phenyl-3,4,5,6-tetrahydro-2H-1,3,5-thiadiazin-4-one), and Fenoxycarb (ethyl 2-(4-phenoxyphenoxy)ethylcarbamate).

In one embodiment, the agricultural chemical comprises at least one bactericide, fungicide or virucide that is effective against a particular bacteria, fungus or virus can be incorporated into the compositions described herein and applied to a desired crop or situs. Suitable non-limiting examples of suitable bactericide and fungicides include Dithane (zinc ethylenebis(dithiocarbamate)), Maneb (manganese ethylenebis (dithiocarbamate)), Thiram (bis(dimethylthiocarbamoyl) disulfide) Manzeb (complex of zinc and manganese ethylenebis(dithiocarbam-ate), Bisdithane (bisdimethyl dithiocarbamoyl zinc ethylene bisdithiacarbamate), and Propineb (polymeric zinc propylenebis(dithiocarb-amate), benzimidazole-based bactericides including Benomyl (methyl1-(butyl-carbamoyl)-2-benzimidazole carbamate) and Thiophanate-methyl (dimethyl(4,4'-o-phenylenebis(3-thioallophanate)), and Vinclozolin (3-(3,5-dichlorophenyl)-5-methyl-5-vinyl-1,3-oxazolidine2,4-dione), Iprodione (3-(3,5-dichlorophenyl)-N-isopropyl-2,4-dioxoimidazolidine-1-carboxamide), Procymidone (N-(3,5dichlorophenyl)-1,2-dimethylcyclo-prop-ane-1,2-dicarboximide), Anilazine (2,4-dichloro-6-(o-chloroanilino)-1,3,5-triazine), Triflumizole ((E)-4-chloro-α-trifluoro-N-(1-imidazol-1-yl-2-propoxyethylidene)o-toluidine), Metalaxyl (methyl-N-(2-methoxyacetyl)-N-(2,6-xylyl)-DIL-alaninate), Bitertanol (all-rac-1-(biphenyl-4-yloxy)-3,3-dimethyl-1-(1,2,4-triazol-1-yl)butan-2-o 1), Pyrifenox (2',4'-dichloro-2-(3-pyridyl)acetophenone-(EZ)-O-methyloxime), Fenarimol (2,4'-dichloro-.alpha.-(pyrimidin-5yl)benzhydryl-alcohol), Triforine (1,4-bis-(2,2,2-trichloro-1-formamidoethyl)-piperazine-), Guazatine iminoctadine (1,1-iminiodi(octamethylene)diguanidinium triacetate), Oxine-copper, antibiotic bactericides (streptomycin type, tetracycline type, polyoxins type, blasticidin S type, kasugamycin type, and validamycin type), Triadimefon (1-(4-chlorophenoxy)-3,3-dimethyl-1-(1-,2,4-triazol-1-yl)-2-butanone), Isoprothiolane (diisopropyl-1,3-dithiolan-2-ylidenemalanate), Daconil (tetrachloroisophthalonitrile), Pansoil (5-ethoxy-3-trichloromethyl-1,2,4-thiadiazole), Fthalide (4,5,6,7-tetrachlorophmalide), Kitazin-P (0,0-diisopropyl-phosphorothioat-e), Hinosan (ethyl S,S-diphenylphosphorodithioate), Probenazole (3-allyloxy-1,2-benzisothiazol 1,1-dioxide), Captan (N-(trichloromethylthio)-4-cyclohexene-1,2-dicarboximide), Fosetyl (aluminum tris (ethylphosphonate)), and quaternary ammonium compounds. In a particularly preferred embodiment, the fungicide is thiophanate-methyl can be utilized in an amount of between 0.1% and 40% by weight.

In one embodiment, the adjuvant composition or composition comprising at least one agricultural chemical further comprises at least one pigment inhibitor alone or in combination with other pigment inhibitors. In another embodiment, at least one grass meristem destroyer is present. Suitable non-limiting examples include aryloxyphenoxypropionates or cyclohexanediones.

In one embodiment, the adjuvant composition or composition comprising at least one agricultural chemical further comprises at least one acaricide. Suitable non-limiting examples include Sumiito (2-tert-butyl-5-(4-tert-butylbenzylthio)-4-chloropyridazi-ne-3-(2H)-one), Acricid (2,4-dinitro-6-sec.-butylphenyldimethylacrylate), Chloromite (isopropyl 4,4-dichlorobenzylate), Akar (ethyl 4,4'-dichlorobenzilate), Kelthane (2,2,2trichloro-1,1-bis(p-chlorophenyl)-ethanol), Citrazon (benzoic 3-chloro-N-ethoxy-2,6-dimethoxybenzimidic anhydride), Omite (2-(p-tert-butylphenoxy)cyclohexyl propyn-2-yl sulfite), Osadan (bis[tris(2-methyl-2-phenylpropyl)tin]oxide), Hexythiazox (trans-5-(4-chlorophenyl)-N-cyclohexyl-4-methyl-2-oxothiazol-idine-3-carbox amide), and Amitraz (N,N-bis(2, 4-xylyliminomethyl)methylamine).

In one embodiment, the adjuvant composition or composition comprising at least one agricultural chemical further comprises at least one transfection agent. There are numerous known transfection agents, any of which can be used in the compositions described herein. In one embodiment, the transfection agents are used in combination with genetic material to be transfected into a cell, and optionally, an appropriate vector, for example, an adenoviral vector. In one embodiment, the genetic material can be any genetic material capable of effecting a desired alteration in the plant genetic code, and can be in the form of a plasmid. In a preferred embodiment, the genetic material is DNA.

In one embodiment, the adjuvant composition or composition comprising at least one agricultural chemical further comprises at least one wood treatment chemical capable of inhibiting destruction of wood by termites, fungus, and mold. Suitable non-limiting examples of suitable wood treatment chemicals include CCA, polyethylene glycol, fungicides, termiticides, and known fungicides.

In one embodiment, the adjuvant composition or composition comprising at least one agricultural chemical further comprises at least one trap for controlling insect populations. In one embodiment, the at least one trap may include a chemical that attracts a desired insect, for example, a pheromone or other insect attractant, and also typically include an insecticide. In one embodiment, the at least one trap is used for controlling populations of burrowing insects, flying insects or crawling insects, for example, roaches, ants, Japanese beetles, termites, mosquitoes and many other insects. The traps as described herein may further include a permeabilizer to enhance the ability of the insecticide to control the insects in one embodiment.

In one embodiment, the adjuvant composition or composition comprising at least one agricultural chemical further comprises at least one disinfectant or antibacterial agent. Suitable non-limiting examples of suitable disinfectants/antibacterial agents include quaternary ammonium salts, captan alcohols, essential oils, organic acids, triazines phenols, iodine halo and nitro phenols. Other suitable non-limiting examples include isothiozolones, terpenes, acridines esters of para-hydroxybenzoic acid, aldehydes, aromatic diamidines, biguanidines, anionic surfactants, nonionic surfactants, betaines, quinines, quinolines, hydrogen heroxide, peracetic acid, heavy metal derivatives, derivatives of 1,3 dioxane, derivatives of imidazole, and derivatives of hexamine.

In one embodiment, the compositions described herein can be used in a paint formulation that, optionally, includes permeabilizing agents and also includes wood preservation chemicals, thereby further stabilizing the wood. In one embodiment, the compositions are added to house paints which typically include an aqueous solvent and a latex material.

In one embodiment, the adjuvant composition or composition comprising at least one agricultural chemical further comprises at least one suspension aid. In a preferred embodiment, the adjuvant composition comprises between 0.1% and 10% by weight of a suspension aid such as, for example, xanthum gum which is marketed as RHODOPOL 23 and manufactured by Rhodia, Inc of Cranbury, N.J. In a particularly preferred embodiment, the compositions comprise about 0.2% of at least one suspension aid such as xanthum gum.

In one embodiment, the adjuvant composition or composition comprising at least one agricultural chemical further comprises at least one organic biocide. In a preferred embodiment, the compositions may comprise a mixture of bicycle oxazolidines such as that marketed as NUOSEPT 95 and manufactured by International Specialty Products. Preferably, the compositions comprise between 0.1% and 5% by weight of the at least one biocide. In a particularly preferred embodiment, the compositions comprises about 0.2% of at least one biocide.

In one embodiment, the adjuvant composition or composition comprising at least one agricultural chemical further comprises at least one antifoam agent. In a preferred embodiment, the antifoam agent is a silicone antifoam emulsion (organic-inorganic mixture) such as that available from Harcos Chemicals, Inc. Preferably, the antifoam agent is present in an amount of between 0.1% and 5%. In a particularly preferred embodiment, the antifoam agent is present in an amount of about 0.2% by weight.

In one embodiment, the adjuvant composition or composition comprising at least one agricultural chemical further comprises at least one flow agent. In one embodiment, any flow agent that is able to minimize or avoid caking of the composition can be used. In one embodiment, the adjuvant composition comprises between 0.1% and 10% by weight of at least one flow agent. Suitable non-limiting examples of suitable flow agents include silica gels; both fumed and precipitated and clays such as kaolin, talc, diatomaceous earth. In a preferred embodiment, the adjuvant composition may comprise propylene glycol in an amount of between 0.1% and 10%. In a particularly preferred embodiment, the adjuvant composition comprises about 2% by weight of propylene glycol.

In one embodiment, the adjuvant composition or composition comprising at least one agricultural chemical further comprises at least one surface active component or surfactant. Suitable non-limiting examples of suitable surface active compounds or surfactants include polyalkylene oxide polymers, such as block polymers. Specific non-limiting examples include polyoxyethylene polyoxypropylene block polymers, and polyoxyethylene polyoxypropylene block polymer ethers such as a polyoxypropylene-polyethylene block copolymer marketed as PLURONIC L62 and manufactured by BASF. Another suitable example is the surfactant marketed as PLURONIC P-104 and manufactured by Ethox Chemicals, LLC of Greenville, S.C. In a preferred embodiment, the compositions comprise between 0.1% and 5% by weight of at least one surface active component. In a particularly preferred embodiment, the compositions comprise about 1.5% by weight of each of at least one of the surface active component or surfactant.

In one embodiment, the adjuvant composition or composition comprising at least one agricultural chemical further comprises at least one suitable acid. In a preferred embodiment, the compositions comprise phosphorous acid or phosphorous acid flakes in an amount of between 0.1% and 5% by weight. In a particularly preferred embodiment, the phosphorous acid is present in an amount of about 8% by weight.

In one embodiment, the adjuvant composition or composition comprising at least one agricultural chemical further comprises at least one suitable base. In a preferred embodiment, the potassium hydroxide is present in an amount of between 0.1% and 35% by weight. In a particularly preferred embodiment, the potassium hydroxide is present in an amount of between 13% and 27% by weight.

In one embodiment, the adjuvant composition or composition comprising at least one agricultural chemical further comprises at least one of a variety of optional components alone or in combination. In one embodiment, at least one additional, optional component can be introduced into the compositions. Such additional components include other agricultural chemicals, flow agents, preservatives, buffering agents, antifoam agents, compatibility agents, crop oil concentrates, deposition agents, dispersants, drift control agents, penetrants, surfactants, spreaders, and wetting agents.

In one embodiment, the compositions can be prepared in solid form by mixing the components, for example, using a blender, fitzmill or other suitable apparatus. In a preferred embodiment, the solid formulations include a flow agent. In one embodiment, at least one flow agent is advantageously added to the solid components in a suitable amount to promote even flow of the material.

In one embodiment, the compositions can also be prepared in liquid form, by adding the components to a desired solvent or dispersant. In one embodiment, at least one dispersant can be, for example, a crop oil, water, or an aqueous solution including water soluble organic solvents such as ethanol. In another embodiment, the adjuvant composition or composition comprising at least one agricultural chemical can be prepared as dispersions in a liquid either singly or as combinations with other suspensions or solutions of other permeabilizers.

In one embodiment, the at least one agricultural chemical listed above may be present in a concentration at a level well above what is typically required when applied alone. Such embodiment preferably includes at least one permeabilizing agent as well as at least surfactant, acid, base, antifoaming agent, and biocide either alone or in combination. The at least one permeabilizing agent is present at levels that affect the activity of the active ingredient by increasing the permeability across the plant cell wall in a preferred embodiment.

In one embodiment, the at least one permeabilizing agent is utilized at relatively low concentrations, for example, less than 5% by weight, more typically, between 0.5 and 3.0 percent by weight. In one embodiment, the at least one permeabilizing agent functions by bringing aqueous and non-aqueous phases together. In an alternative embodiment, the at least one permeabilizing agent is utilized at relatively higher concentrations, i.e., greater than 5% by weight, more preferably greater than 10% by weight and most preferably about 20% by weight. In such an embodiment, the at least one permeabilizing agent not only brings aqueous and non-aqueous phases together, but also enhances the ability of the at least one agricultural chemical to cross plant cell walls.

In one embodiment, all compositions can be generally applied to a plant in need of treatment thereof in an effective amount to effect such treatment. The compositions can be applied by conventional application techniques. These techniques include, but are not limited to, root application, leaf application, crop dusting, or spray application. In one embodiment, the compositions can be used with coatings; for example wood treatment, paint, or other surface treatments.

In another embodiment, the compositions can be used to treat a plant with a pesticide, herbicide, insecticide, fungicide, virucide, bactericide, or acaricide or a combination thereof. In one embodiment, the methods involve applying to the plant an effective pesticidal, herbicidal, insecticidal, fungicidal, virucidal, bactericidal, or acaricidal amount of a composition including a permeabilizing agent and a pesticide, herbicide, insecticide, fungicide, virucide, bactericide, or acaricide or a combination thereof. In other embodiments, the compositions are used to effectuate weed management, disease control or insect management or a combination thereof.

In one embodiment, formulations described herein can also be used to enhance the results obtained with conventional weed control formulations. Weed control essentially involves applying a compound that selectively controls one type of plant in the presence of another. Suitable non-limiting examples include crabgrass-selective compounds that have little or no effect on grass. In one embodiment, weed control agents can be combined with the permeabilizing agents described herein to form enhanced weed control agents, enhanced due to their ability to permeate through the cell walls of the undesired weeds. In all of these embodiments, the chelating agents are typically the sugars, acids and salts of maleic acid, malonic acid, tartaric acid, citric acid, glycine, lactic acid, malic acid, succinic acid, oxalic acid, dextrose, ethylenediaminetetraacetic acid (EDTA), tris(hydroxymethyl)aminomethane, lactose, mannitol, glutaric acid, malic acid, succinic acid, glycerol, humic acid, fulvic acid, sorbic acid, sorbose, ethylene diamine, 1,2 diaminocyclohexane, trimethylenediamine, tetramethylenediamine, 1,2 diaminopropane, diethylenetriamine, triethylenetetramine, triaminodiethylamine, N-hydroxyethylethylenediamine-, some quaternary ammonium salts, dimethyl amines, and agriculturally acceptable salts thereof, and mixtures thereof.

In addition to the benefit of increased permeation, the chelation of calcium ions has a beneficial effect on auxins. In one embodiment, defoliation and boll opening are the result of a combination of plant hormones including, but not limited to, ethylene and auxins, either alone or in combination. In one embodiment, these two hormones have opposing effects on the plant for many processes. In one embodiment, ethylene causes ripening, abscission, and. senescence. In another embodiment, auxin inhibits these processes. In one embodiment, auxin may be used in combination with calcium ions for efficient transport. In one embodiment, inorganic solutes, and specifically calcium, can affect the action of hormones and exogenous growth regulators. The application of chelators, specifically calcium chelators, can slow the transport of auxin and enhance the action of exogenous active components in one embodiment.

In one embodiment, the at least one chelating agent application rate used in the defoliation method ranges from about 0.1 pound per acre to about 5 pounds per acre, preferably from about 0.25 to about 2.5 pounds per acre. The chelating agents can be used and/or applied with paraquat, diquat, endothall, chlorates, ethephon, tributylyphosphorothioate, cacodylic acid and its sodium salt, MSMA, diuron, dimethipin, monocarbamide, carfentrazone, cyclanalide and thidiazuron in ratios from 1:100 to 100:1, preferably from 1:10 to 10:1.

EXAMPLES

Example 1

Evaluation of Fungicide for Control of Leafspot on Peanuts

This example evaluated the effectiveness of the fungicides chlorothalonil and praclostrobin for control of black spot on peanuts. The fungicides were tested alone and in combination with an adjuvant composition. A control (untreated) portion was also monitored for black spot. The compositions utilized are summarized as follows:

Composition #1

| Raw Material | Weight % |
| --- | --- |
| Water | 23.91% |
| Potassium Hydroxide (45%) | 15.42% |
| Phosphorous Acid Flakes | 7.87% |
| Pluronic P-104 | 1.5% |
| Pluronic L62 | 1.5% |
| Antifoam | 0.2% |
| Nuosept 95 | 0.2% |
| Ameen DMCD | 2% |
| EDTA Tetrasodium | 20% |
| Propylene Glycol | 2% |
| Rhodopol 23 | 0.2% |

Composition #2

| Raw Material | Weight % |
| --- | --- |
| Water | 27.83% |
| Potassium Hydroxide (45%) | 23.50% |
| Phosphorous Acid Flakes | 7.87% |
| Pluronic P-104 | 1.5% |
| Pluronic L62 | 1.5% |
| Antifoam | 0.2% |
| Nuosept 95 | 0.2% |
| Armeend DMCD | 2% |
| Citric Acid | 8.0% |
| Propylene Glycol | 2% |
| Rhodopol 23 | 0.2% |

The experimental data obtained is summarized below. The ratings were made on a Florida Scale with a higher number indicating more advanced disease. The rating was observed at approximate two months after emergence.

| Treatment | Rate | Rate Unit | Rating of Disease (1-10) | Yield |
| --- | --- | --- | --- | --- |
| Untreated | | | 9 | 3080 |
| Fungicide (chlorothalonil) | 1.37 | lb/acre | 4.875 | 4479 |
| Praclostrobin | 6 | fl oz/ac | | |
| Fungicide (chlorothalonil) | 1.37 | lb/acre | 4.625 | 4536 |
| Praclostrobin | 6 | fl oz/ac | | |
| Adjuvant #1 (see above) | 0.75 | % v/v | | |
| Fungicide (chlorothalonil) | 1.37 | lb/acre | 4.688 | 4455 |
| Praclostrobin | 6 | fl oz/ac | | |
| Adjuvant #2 (see above) | 0.75 | % v/v | | |

The application of the adjuvant composition resulted in enhanced leafspot control compared to addition of the fungicide, alone, or when the plants were left untreated. The composition did not harm peanut yield.

Example 2

Evaluation of Fungicide for Control of Black Spot on Roses

This example evaluated the effectiveness of the fungicide thiophanate methyl for the control of black spot on roses. The fungicide was mixed with water in a spray tank at the listed rate treatment (A), or with a permeabilizer (B) and the degree of control of the blackspot was evaluated. The ratings were made after one week on the per cent leaves infected with blackspot. The data show that the fungicide was only slightly effective in the absence of permeabilizer (20%), but extremely effective (68%) in the presence of the permeabilizer.

A. Thiophanate Methyl—1 oz/gal
B. Thiophanate Methyl—1 oz/gal+Adjuvant 1 80 g/gal
Fungicidal Efficiency % Control
Black Spot Roses
A. 20%
B. 68%

Example 3

Effectiveness of a Bactericide on Bacterial Leaf Spot (*Xanthomonas campestris*) on Tomatoes This example evaluated the effectiveness of the bactericide copper hydroxide for the control of bacterial leaf spot on tomatoes. The tomato plants were inoculated with the bacteria. The bactericide was mixed with water in a spray tank at the listed rate treatment (A), or with a permeabilizer (B) and the degree of control of the leaf spot was evaluated. The ratings were made after two weeks on the per cent leaves infected.

| Treatment | % Leaves Infected |
| --- | --- |
| Copper 2#/acre | 63% |
| Copper 1#/ac + Adjuvant (in water - included 20% EDTA salt, 5% dicocodimethylammonium chloride, 1% cocodimethylamine, and 7% propylene glycol)(300:1 dilution) | 46% |

The data show that the presence of the adjuvant enhanced the effectiveness of the bactericide. Only about one third of the leaves treated with bactericide alone were uninfected, in comparison to more than half of the leaves treated with the combination of bactericide and adjuvant.

Example 4

Evaluation of Fungicide in the Treatment of Early Blight (*Alternaria solani*)

This example evaluated the effectiveness of the fungicide chlorothalonil for the control of Early Blight on tomatoes. The fungicide was mixed with water in a spray tank at the listed rate treatment (A), or with a permeabilizer (B) and the degree of control of the Early Blight was evaluated. The tomato plants were inoculated with the fungi. The ratings were made after one week on the per cent leaves infected with Alternaria and also the number with severe damage—necrosis.

| Leaflets | Infected Leaves | Infected Leaflets | Leaves with >50% Necrosis |
|---|---|---|---|
| Chlorothalonil 2.5 pt/ac | 42% | 60% | 42% |
| Chlorothalonil 1.25 pt/ac + (in water - included 20% EDTA salt, 5% dicocodimethylammonium chloride, 1% cocodimethylamine, and 7% propylene glycol) (300:1 dilution) | 14% | 20% | 14% |

The data show that even when half the amount of fungicide was used, there was a significant decrease in the percentage of infected leaflets, infected leaves, and leaflets with less than 50% necrosis.

Example 5

Effectiveness of Bactericide Streptomycin at Controlling Fireblight

This example evaluated the effectiveness of the bactericide streptomycin for the control of fireblight on Southern Crepe Myrtle. The bactericide was mixed with water in a spray tank at the listed rate treatment (A), or with a permeabilizer (B). The infected plants were treated with the bactericide by spraying until wet and the degree of control of the fireblight was evaluated. The ratings were made after two days on the rate required for control.

Level of Control
A. Streptomycin—60 ppm
B. Streptomycin+Adjuvant (in water—included 20% EDTA salt, 5% dicocodimethylammonium chloride, 1% cocodimethylamine, and 7% propylene glycol)(500:1 dilution)—20 ppm The data show that the presence of adjuvant significantly lowered (by a factor of 2 thirds) the amount of bactericide needed to control fireblight.

Having disclosed the subject matter of the present invention, it should be apparent that many modifications, substitutions and variations of the present invention are possible in light thereof. It is to be understood that the present invention can be practiced other than as specifically described. Such modifications, substitutions and variations are intended to be within the scope of the present application. As used in the following claims, articles such as "a", "the" and so on can connote the singular or the plural of the object following.

I claim:

1. An agricultural adjuvant chemical composition effective at increasing effectiveness or efficacy of an agricultural chemical comprising
    0.1% to 5% by weight of at least one acidic compound comprising citric acid and/or phosphorous acid;
    0.1% to 35% by weight of at least one basic compound comprising potassium hydroxide;
    0.1% to 40% by weight of at least one permeabilizing agent;
    0.1% to 10% by weight of at least one alkylamine; and propylene glycol, wherein the remainder of the adjuvant chemical composition comprises water.

2. The adjuvant chemical composition of claim 1 wherein the at least one acid compound is phosphorous acid.

3. The adjuvant chemical composition of claim 1 wherein the at least one acid compound is citric acid.

4. The adjuvant chemical composition of claim 3 wherein the citric acid is present in an amount of 0.1% to 20% by weight.

5. The adjuvant chemical composition of claim 1 wherein the at least one basic compound is potassium hydroxide.

6. The adjuvant chemical composition of claim 1 wherein the at least one permeabilizing agent is a chelating agent.

7. The adjuvant chemical composition of claim 6 wherein the chelating agent is selected from the group consisting of ethylenediaminetetraacetic acid (EDTA), diethylenetriaminepentaacetic acid (DTPA), (hydroxyethyl)ethylenediaminetriacetic acid (HEDTA), nitrilotriacetic acid (NTA), oxalic acid, and citric acid.

8. The adjuvant chemical composition of claim 1 wherein the at least one alkylamine is a fatty acid amine.

9. The adjuvant chemical composition of claim 8 wherein the fatty acid amine is cocoalkylamine.

10. The adjuvant chemical composition of claim 1 further comprising at least one quaternary ammonium salt.

11. The adjuvant chemical composition of claim 10 wherein the at least one quaternary ammonium salt comprises cocodimethylamine, dicocoalkylmethylamine or a combination thereof.

12. The adjuvant chemical composition of claim 1 further comprising 0.1% to 40% by weight of at least one surfactant or surface active component.

13. The adjuvant chemical composition of claim 12 wherein the at least one surface active component comprises at least one polyoxypropylene or polyethylene block copolymer or a combination thereof.

14. The adjuvant chemical composition of claim 1 further comprising 0.1% to 5% by weight of at least one at least one antifoaming agent.

15. The adjuvant chemical composition of claim 14 wherein the at least one antifoaming agent comprises a silicone antifoam emulsion.

16. The adjuvant chemical composition of claim 1 further comprising 0.1% to 5% by weight of at least one at least one biocide.

17. The adjuvant chemical composition of claim 16 wherein the at least one biocide comprises a mixture of bicycle oxazolidines.

18. The adjuvant chemical composition of claim 1 further comprising 0.1% to 10% by weight of at least one at least one suspension aid.

19. The adjuvant chemical composition of claim 18 wherein the at least one suspension aid comprises xanthum gum.

20. The adjuvant chemical composition of claim 1 further comprising 0.1% to 10% by weight of at least one at least one flow agent.

21. The adjuvant chemical composition of claim 20 wherein the at least one flow agent comprises propylene glycol.

22. The adjuvant chemical composition of claim 1 further comprising at least one agricultural chemical.

23. The adjuvant chemical composition of claim 22 wherein the at least one agricultural chemical is selected from the group consisting of a herbicide, fungicide, and plant growth regulator.

24. A composition effective at increasing effectiveness or efficacy of an agricultural chemical comprising
    0.1% to 5% by weight of at least one acidic compound comprising citric acid and/or phosphorous acid;

0.1% to 35% by weight of at least one basic compound comprising potassium Hydroxide;

0.1% to 40% by weight of at least one permeabilizing agent;

0.1% to 10% by weight of at least one alkylamine propylene glycol; and at least one agricultural chemical, wherein the remainder of the adjuvant chemical composition comprises water.

25. The composition of claim 24 wherein the at least one acid compound is phosphorous acid.

26. The composition of claim 24 wherein the at least one acid compound is citric acid.

27. The composition of claim 26 wherein the citric acid is present in an amount of 0.1% to 20% by weight.

28. The composition of claim 24 wherein the at least one basic compound is potassium hydroxide.

29. The composition of claim 24 wherein the at least one permeabilizing agent is a chelating agent.

30. The composition of claim 29 wherein the chelating agent is selected from the group consisting of ethylenediaminetetraacetic acid (EDTA), diethylenetriaminepentaacetic acid (DTPA), (hydroxyethyl)ethylenediaminetriacetic acid (HEDTA), nitrilotriacetic acid (NTA), oxalic, and citric acid.

31. The composition of claim 24 wherein the at least one alkylamine is a fatty acid amine.

32. The composition of claim 31 wherein the fatty acid amine is cocoalkylamine.

33. The composition of claim 24 further comprising at least one quaternary ammonium salt.

34. The composition of claim 33 wherein the at least one quaternary ammonium salt comprises cocodimethylamine, dicocoalkylmethylamine or a combination thereof.

35. The composition of claim 24 further comprising 0.1% to 40% by weight of at least one surfactant or surface active component.

36. The composition of claim 35 wherein the at least one surface active component comprises at least one polyoxypropylene or polyethylene block copolymer or a combination thereof.

37. The composition of claim 24 further comprising 0.1% to 5% by weight of at least one at least one antifoaming agent.

38. The composition of claim 37 wherein the at least one antifoaming agent comprises a silicone antifoam emulsion.

39. The composition of claim 24 further comprising 0.1% to 5% by weight of at least one at least one biocide.

40. The composition of claim 39 wherein the at least one biocide comprises a mixture of bicycle oxazolidines.

41. The composition of claim 24 further comprising 0.1% to 10% by weight of at least one at least one suspension aid.

42. The composition of claim 41 wherein the at least one suspension aid comprises xanthum gum.

43. The composition of claim 24 further comprising 0.1% to 10% by weight of at least one at least one flow agent.

44. The composition of claim 43 wherein the at least one flow agent comprises propylene glycol.

45. The composition of claim 24 further comprising at least one agricultural chemical, wherein the at least one agricultural chemical is selected from the group consisting of a herbicide, fungicide, and plant growth regulator.

* * * * *